(12) United States Patent
Lee et al.

(10) Patent No.: US 6,187,271 B1
(45) Date of Patent: Feb. 13, 2001

(54) ELECTROSTATIC PRECIPITATOR

(75) Inventors: Sung Hwa Lee; Young Ki Hong; Kwang Ok Kang; Soo Yeon Shin; Kyeng Wook Heo; Jung Hun Kang, all of Kyungsangnam-do (KR); Akira Mizno, Aiji-ken (JP)

(73) Assignee: LG Electronics, Inc., Seoul (KR)

( * ) Notice: Under 35 U.S.C. 154(b), the term of this patent shall be extended for 0 days.

(21) Appl. No.: 09/137,241

(22) Filed: Aug. 20, 1998

(30) Foreign Application Priority Data

Aug. 21, 1997 (KR) .................................................. 97-39824
Aug. 21, 1997 (KR) .................................................. 97-39827

(51) Int. Cl.[7] ...................................................... A62B 7/08
(52) U.S. Cl. .................................. 422/121; 96/16; 96/69; 96/223; 96/225; 422/22; 422/122
(58) Field of Search ..................................... 422/121, 122, 422/24, 22; 96/16, 69, 223, 225

(56) References Cited

U.S. PATENT DOCUMENTS

| 5,151,252 | 9/1992 | Mass ................................. 422/186.3 |
| 5,397,552 | 3/1995 | Weigold et al. .................. 422/186.3 |
| 5,707,428 | * 1/1998 | Feldman et al. ........................ 96/54 |

FOREIGN PATENT DOCUMENTS

| 10-61986 | * 3/1998 | (JP) . |
| WO 97/09073 | 3/1997 | (WO) . |

* cited by examiner

Primary Examiner—Krisanne Thornton
(74) Attorney, Agent, or Firm—Fleshner & Kim, LLP

(57) ABSTRACT

Electrostatic precipitator is disclosed, including a discharge unit having ground electrodes and discharge electrodes, and a collecting unit having collecting electrodes and positive electrodes, wherein the discharge unit is applied of a voltage enough to emit a photo-energy which can activate a photo-catalyst, and a component in the electrostatic precipitator contains the photo-catalyst, or a separate photo-catalyst filter containing the photo-catalyst is provided within a reach of the photo-energy emitted from the discharge unit , thereby the photo-energy from the discharge unit activating the photo-catalyst, whereby providing a simple structured electrostatic precipitator making sterilization and deodorization at a low cost.

21 Claims, 7 Drawing Sheets

ELECTROSTATIC PRECIPITATOR

BACKGROUND OF THE INVENTION

1. Field of the Invention

The present invention relates to an electrostatic precipitator, and more particularly, to an electrostatic precipitator, in which a photo-catalyst technology is utilized for sterilization and deodorization.

2. Discussion of the Related Art

In general, the electrostatic precipitator collects and removes solid state, and liquid state particles floating in a gas. FIG. 1 illustrates a section of a background art electrostatic precipitator, with reference to which the background art electrostatic precipitator will be explained.

The background art electrostatic precipitator is provided with a body 10 having an intake grill 12 and a discharge grill 14, and filters 20, 30, and 100 and fan 16 mounted inside of the body 10. In the filters, there are a pre-filter 20 at rear of the intake grill 12 for primary filtering of dusts from intake air, an electrostatic precipitating part 100 at rear of the pre-filter 20 for electrical removal of dusts, deodorizing filter 30 at rear of the electrostatic precipitating part 100 for removal of odor in air.

The foregoing electrostatic precipitator will be explained in detail with reference to FIG. 2. The electrostatic precipitating part 100 is provided with the discharge unit 110 for charging dusts and the like in air, and the collecting unit 130 for collecting the dusts charged in the discharge unit 110. In detail, the body 10 has a discharge unit case 112 and holders 114 on both sides of the discharge unit case 112. And, there are a plurality of ground electrodes 116 fitted to the holders 114 at fixed intervals, and a plurality of discharge electrodes 118 between the ground electrodes 116. And, the body 10 has a collecing case 132 which has a plurality of collecting electrodes 134 fitted thereto at fixed intervals for acting as ground electrodes, and there are a plurality of positive electrodes 136 between the collecting electrodes 134. A plurality of projections 138 may be provided on top of both the collecting electrodes 134 and the positive electrodes 136 for maintaining a gap between the electrode plates 134 and 136. The collecting electrodes 134 and the positive electrodes 136 are conductors, such as conductive paint or aluminum foil. Resin of a good insulating property is coated or bonded on the conductors.

At time, there is a metal mesh(not shown) between a discharge unit 110 and a collecting unit 130 for minimizing electric field interference between the discharge unit 110 and the collecting unit 130.

In the meantime, there are a "−" voltage applying terminal 142 and a "+" voltage applying terminal 144; the "−" voltage applying terminal 142 is connected to the ground electrodes 1 16 in the discharge unit 110 and the collecting electrodes 134 in the collecting unit 130, and the "+" voltage applying terminal 144 is connected to the discharge electrodes 118 and the positive electrodes 136.

The operation of the background art electrostatic precipitator will be explained with reference to FIGS. 1 and 2.

Upon application of power to the electrostatic precipitator, the fan 16 is put into operation to cause outside air to flow into the body 10 through the intake grill 12. The air is primarily filtrated of comparatively large sized dusts as the air passes through the prefilter 20 and flows to the discharge unit 110. As the ground electrodes 116 and the discharge electrodes 118 in the discharge unit 110 are at application of voltage, a corona discharge occurred between the ground electrodes 116 and the discharge electrodes 118, charging dust particles flowed in the discharge unit 110. The dusts charged in the discharge unit 110 continues to flow toward the collecting unit 130, where, as the charged dusts are charged of "+", a repulsive force is acted between the dusts and the positive electrodes 136 having a "+" voltage applied thereto, and an attracting force is acted between the dusts and the collecting electrodes 134 having a "−" voltage applied thereto. Accordingly, the charged dusts are accelerated toward the collecting electrodes 134, being collected at the collecting electrodes 134 at last. The air, passed through the collecting unit 130 finally, is removed of odors in the air as the air passes through the deodorizing filter 30 of active carbon, to become clean air, which is discharge through the discharge grill 14. However, the background art electrostatic precipitator can not remove harmfull microbes contained in the air, and has a poor deodorizing performance, causing a problem that the harmful microbes are discharged into a room without being filtrated, or accumulated on electrode plates in the collecting unit 130 and decomposes to give out bad smell.

To cope with this problem, so called photo-catalyst technology is developed, in which a substance (hereafter called "photo-catalyst") adapted to be activated by a photo-energy to have sterilizing and deodorizing capability is used, of which typical photo-catalyst is titanium oxide $TiO_2$. The photo-catalyst like titanium oxide has an excellent adsorption power to organic substances and is excited when exposed to a photo energy to form various forms of radical, which sterilizes microbes by a strong oxidation power and, on the same time, decomposes substances giving out bad smells in reaction with the radical.

This may be explained in detail referring to FIG. 3 as follows.

When a photo-energy emitted from an UV lamp and the like is directed onto a photo-catalyst, an electron in a valence band is transited to a conduction band, generating an electron and a hole. As these electron and hole have very strong oxidizing and reducing power, these electron and hole make reaction with water vapor $H_2O$ or oxygen $O_2$ in air, to produce active oxygens, such as OH radical, H radical, and super oxide n ion $O_2^-$. And, as these radicals have strong bonding forces to other components, these radicals break bonding of substances giving a bad smell, thereby making deodorization. That is, as OH radical breaks bonding of an organic substance which causes an odor and makes a direct bonding with the organic substance, leaving water vapor and carbon dioxide finally, the odor is removed. And, as OH radical has a strong oxidizing power which sterilizes microbes, OH radical can sterilize microbes. When the electron or hole make a direct bonding with organic substance, the direct bonding breaks bonding of the organic substance, changing the organic substance to another form of radical. And, the another form of radical breaks a bonding of another organic substance, to form water vapor and carbon dioxide at the end, thereby making deodorization. Thus, by proceeding the foregoing process, sterilization and deodorization can be made.

PCT application(PCT/US 96/14204) discloses a filter coated with a photo-catalyst and a UV lamp which activates the aforementioned photo-catalyst. However, the technologies on sterilization and deodorization using photo-catalyst known up to now have the following problems.

First, as a photo-energy is required for exciting a photo-catalyst as titanium oxide, a separate photo-energy source for generating such a photo-energy has been required additionally. That is, the UV lamp and the like used additionally as the photo-energy source increases components in the electrostatic precipitator, making the electrostatic precipitator to have a complicated structure and to cost high.

Second, the UV lamp or filter coated with photo-catalyst mounted in air stream make resistance to air flow, which causes a pressure loss of the air flow.

SUMMARY OF THE INVENTION

Accordingly, the present invention is directed to an electrostatic precipitator that substantially obviates one or more of the problems due to limitations and disadvantages of the related art.

An object of the present invention is to provide an electrostatic precipitator which has a simple structure and can make sterilization and deodorization at a low cost.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the electrostatic precipitator includes a discharge unit having ground electrodes and discharge electrodes, and a collecting unit having collecting electrodes and positive electrodes, wherein the discharge unit is applied of a voltage enough to emit a photo-energy which can activate a photo-catalyst, and a catalyst filter containing the photo-catalyst is provided within a reach of the photo-energy emitted from the discharge unit, thereby the photo-energy from the discharge unit activating the photo-catalyst.

In other aspect of the present invention, there is provided an electrostatic precipitator including a discharge unit having ground electrodes and discharge electrode, and a collecting unit including collecting electrodes and positive electrodes, wherein the discharge unit is applied of a voltage enough to emit a photo-energy which can activate a photo-catalyst, and a component in the electrostatic precipitator contains the photo-catalyst, the component being within a reach of the photo-energy emitted from the discharge unit, thereby the photo-energy from the discharge unit activating the photo-catalyst.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENT

Reference will now be made in detail to the preferred embodiments of the present invention, examples of which are illustrated in the accompanying drawings.

First Embodiment

Figure 4A:
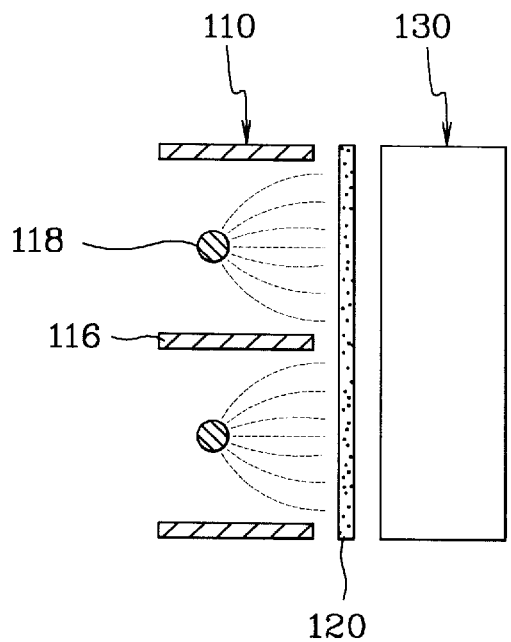
FIGS. 4a and 4b illustrate cross sections of an electrostatic precipitator in accordance with a preferred embodiment of the present invention.

FIG. 4a illustrates a cross section of an electrostatic precipitator in accordance with a preferred embodiment of the present invention. Parts in the present invention identical to the background art will be given the same reference numerals, and explanations on the parts will be omitted.

There is a photo-catalyst filter 120 containing a photo-catalyst between a discharge unit 110 and a collecting unit 130. The photo-catalyst filter 120 has preferably a metal net of, such as aluminum, and a photo-catalyst coated on the metal net. The photo-catalyst filter 120 may be also formed of a mixture of materials, such as the photo-catalyst, aluminum, and other functional materials. The photo-catalyst may be a material activated by a photo-energy, such as $TiO_2$, CDs, $SrTiO_3$, and the like, and preferably a titanium oxide $TiO_2$ having a lattice structure of an anatase phase. For the photo-catalyst being excited, an energy higher than a band gap energy of the photo-catalyst is required, for which a separate external energy source, such as a UV lamp is provided in the background art. However, the subject matter of the present invention is not using the separate energy source. The principle is as follows.

Upon reception of an energy higher than a band gap energy, every substance is involved in state changes from a ground state to an exciting state, and to the ground state, again. When the state of the substance returns to the ground state, the substance emits a band gap energy in a form of photo-energy. In the meantime, researchers in an electrostatic precipitator have paid attention only to that a substance changes a state from a ground state to a excited state by means of an electric discharge, because bringing a substance into an exciting state, i.e., ionizing the substance gives a direct influence to a precipitation efficiency. Therefore, the researches have been focused on the ionization of substance in the discharge unit, and thus using a separate energy source for activation of the photo-catalyst. However, the present invention paid attention to the fact that, when a substance excited in the discharge unit in an electrostatic precipitator returns to a ground state again, the substance emits a photo-energy as much as a band gap energy. As a result, it is confirmed that the photo-catalyst can be activated without the separate energy source if a form or strength of a voltage applied to the discharge unit is adjusted, appropriately.

Figure 1:
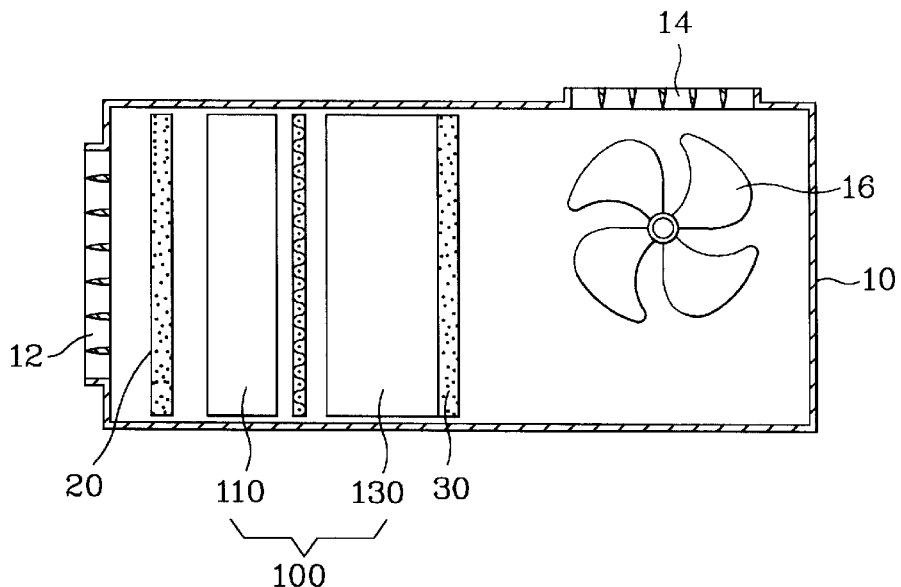
FIG. 1 illustrates a cross-section of a background art electrostatic precipitator.
Figure 2:
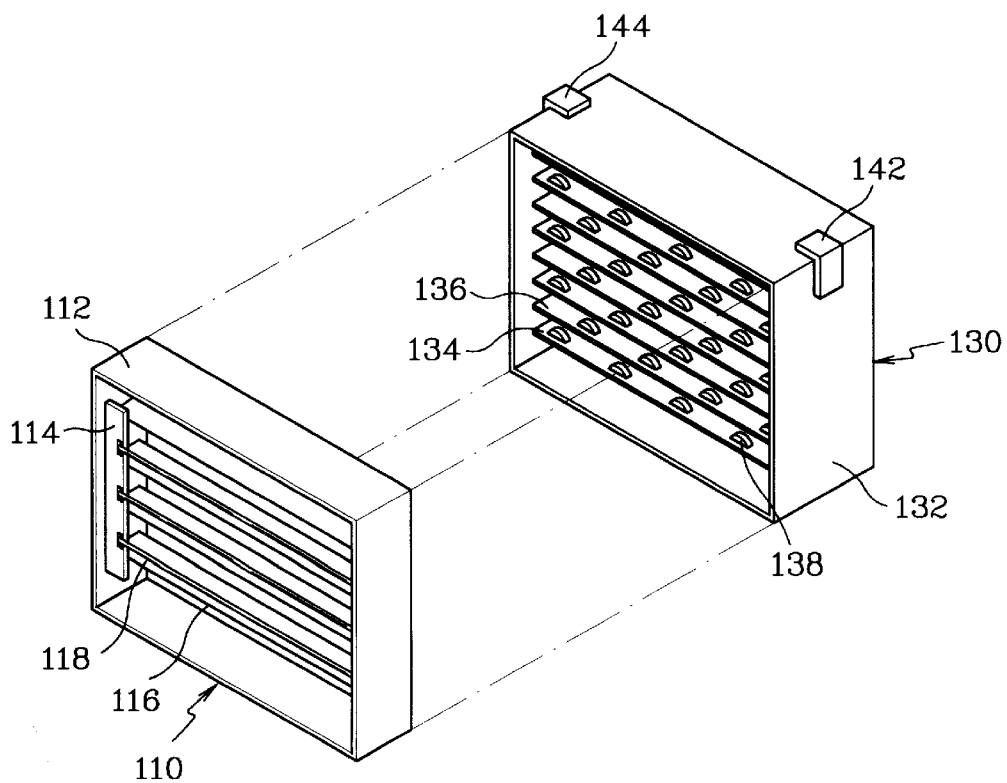
FIG. 2 illustrates a perspective view of an electrostatic precipitator in the background art electrostatic precipitator.
Figure 3:
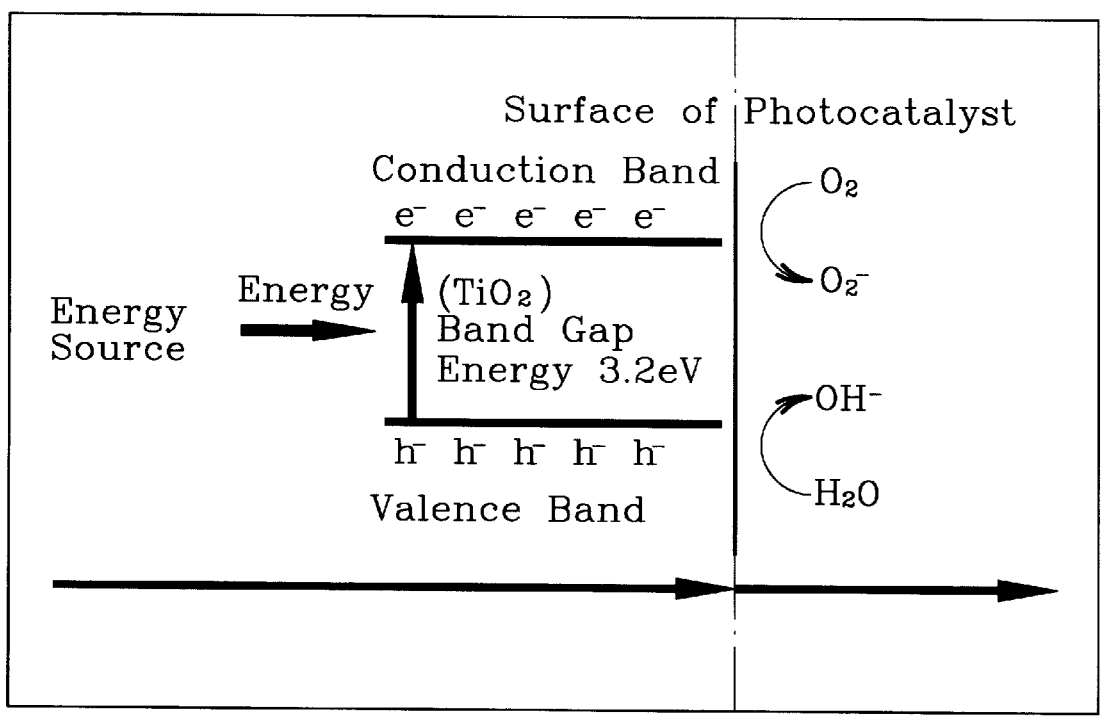
FIG. 3 illustrates a state showing a principle in which a photo-catalyst is made to make reaction by a photo-energy.
Figure 6A:
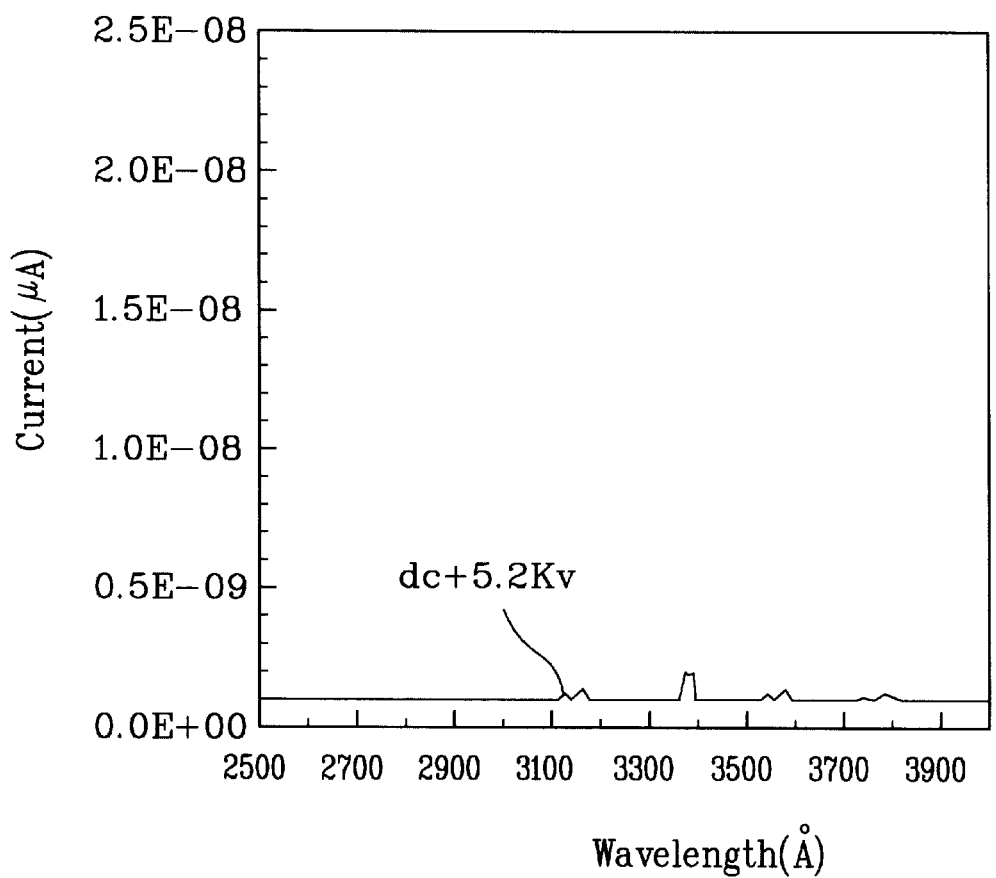
FIGS. 6a and 6b illustrate graphs showing magnitudes of photo-energy emitted from a discharge unit in one embodiment of the electrostatic precipitator of the present invention; and, FIG. 7 illustrates a graph showing a comparison of deodorizing power between the electrostatic precipitators of the background art and the present invention.
Figure 6B:
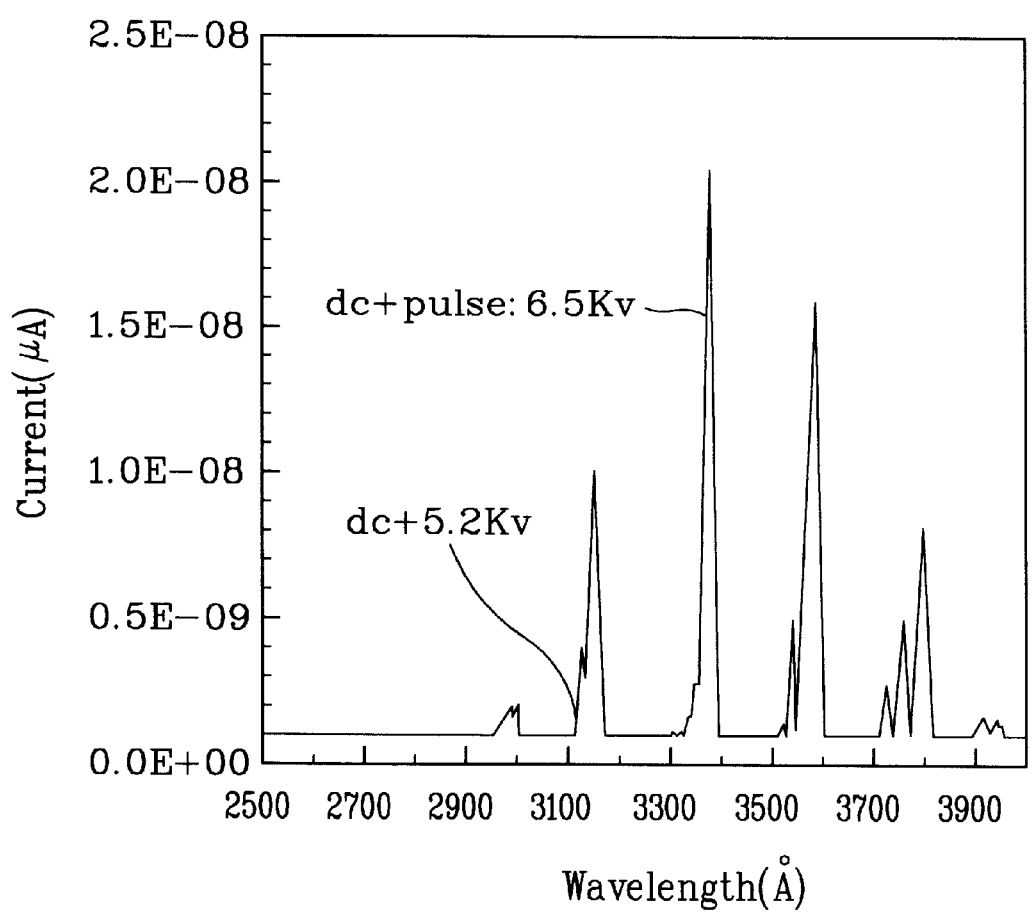

This will be explained in detail with reference to FIGS. 3, 6a and 6b.

A photo-energy(3.2 eV) with a wavelength of approx. 350~400 nm is required for exciting titanium oxide $TiO_2$, a photo-catalyst, to make sterilization and deodorization, and it has been explained that, in the background art photo-catalyst, a separate external energy source, such as an UV lamp is used for obtaining such as photo-energy. However, as shown in FIGS. 6a and 6b, in the present invention, a photo-energy with a wavelength of approx. 3100~3900 Å(310~390 nm) can be obtained by making a high voltage discharge from the discharge unit 110. In FIGS. 6a and 6b, X-axis represents wavelengths of a photo-energy emitted from the discharge unit and Y-axis represents frequencies of wavelengths of the photo-energy. FIG. 6a illustrates a graph showing frequencies of wavelengths of the photo-energy emitted from the discharge unit when the voltage applied to the discharge unit is an DC 5.2 kV, and FIG. 6b illustrates a graph showing frequencies of wavelengths of the photo-energy emitted from the discharge unit when the voltage applied to the discharge unit is a DC biased pulse 6.5 kV. The various molecules in the air have different band gap energies. When discharging in an air, photo-energies of different wavelengths which are continuous are emitted. As can be known from FIGS. 6a and 6b, the DC biased pulse 6.5 kV having a low effective value(about 3.8 kV) compared to the DC 5.2 kV emits a more intensive(having higher peaks) photo-energy. This is because the DC biased pulse 6.5 kV has a higher energy momentarily though the effective value is lower. As can be known from the test result, it is confirmed that a photo-energy greater than a certain magnitude can be obtained from the discharge unit if a high voltage is applied to the discharge unit, and the photo-energy obtained thus is a photo-energy of a magnitude enough to activate the photo-catalyst. And, by changing a form and a magnitude of the voltage applied to the discharge unit, a wavelength and a magnitude of the photo-energy emitted form the discharge unit can be adjusted. Further, it can be known that application of a DC biased pulse is more effective. In conclusion, since the present invention can cause the discharge unit to emit a photo-energy which can activate the photo-catalyst, the photo-catalyst can be activated without a separate external energy source. In the meantime, it can be known that an energy required for activating a photo-catalyst other than titanium oxide, when one is used, can be obtained, and a form and a magnitude of a voltage to be applied to the discharge unit for generating such an energy can be obtained according to the aforementioned test.

Figure 7:
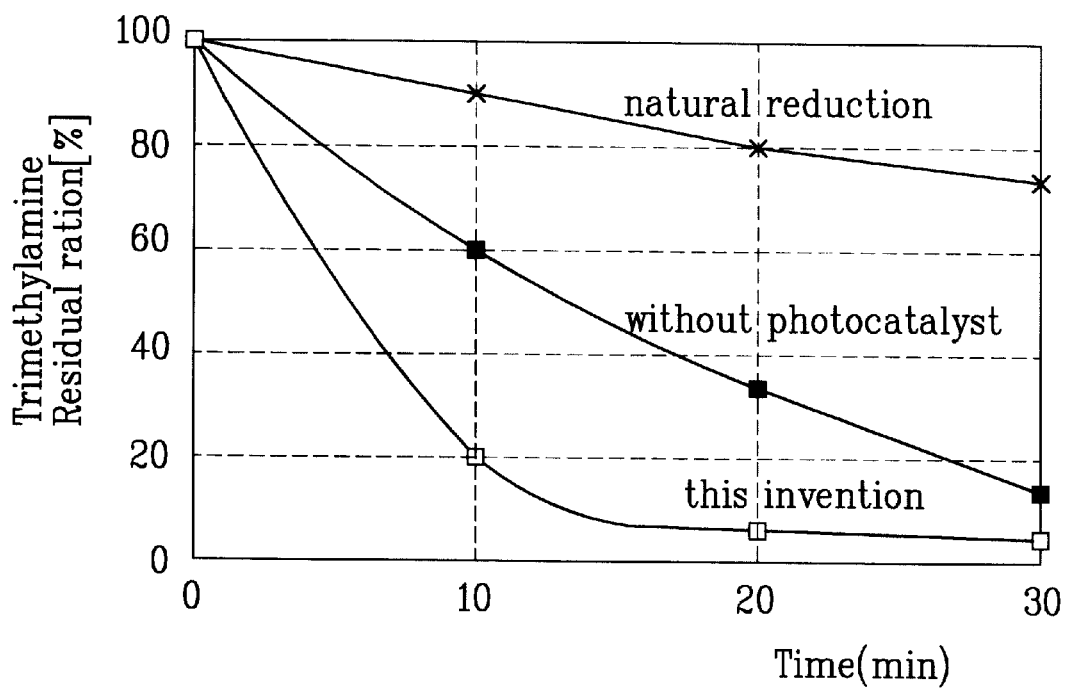

FIG. 7 illustrates a graph showing a comparison of deodorizing power between the electrostatic precipitators of the background art and the present invention based on tri-methyl amine(($CH_3$)$_3$N) which is a major source of a room odor, from which it can be known that the deodorizing power of the electrostatic precipitator of the present invention is substantially excellent compared to the background art electrostatic precipitator.

Advantages of the electrostatic precipitator in accordance with a preferred embodiment of the present invention can be summarized as follows.

First, the possibility of activation of a photo-catalyst without a separate photo-energy source, such as a UV lamp allows to reduced components and simplification of a structure, thereby dropping a production cost.

Second, the non-presence of the UV lamp in the electrostatic precipitator allows to reduce an air pressure loss.

Third, the deodoring efficiency of a room can be improved.

Figure 4B:
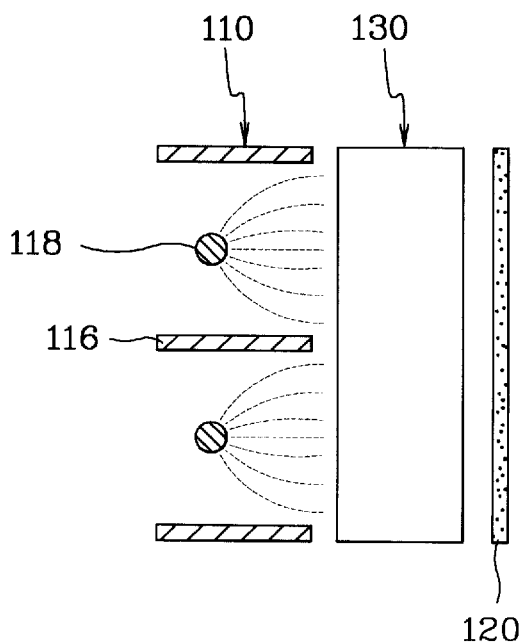

Though, in the first embodiment, a case of the photo-catalyst filter 120 disposed between the discharge unit 110 and the collecting unit 130 is explained, in the present invention, locations of the photo-catalyst filter 120 are not limited to the first embodiment location, but the location of the photo-catalyst filter 120 may be any place wherever the photo-energy of a certain magnitude emitted from discharge electrodes 118 in the discharge unit 110 can reach and activate the photo-catalyst. For example, as shown in FIG. 4b, the photo-catalyst filter 120 may be disposed at rear of the collecting unit 130.

Second Embodiment

Figure 5:
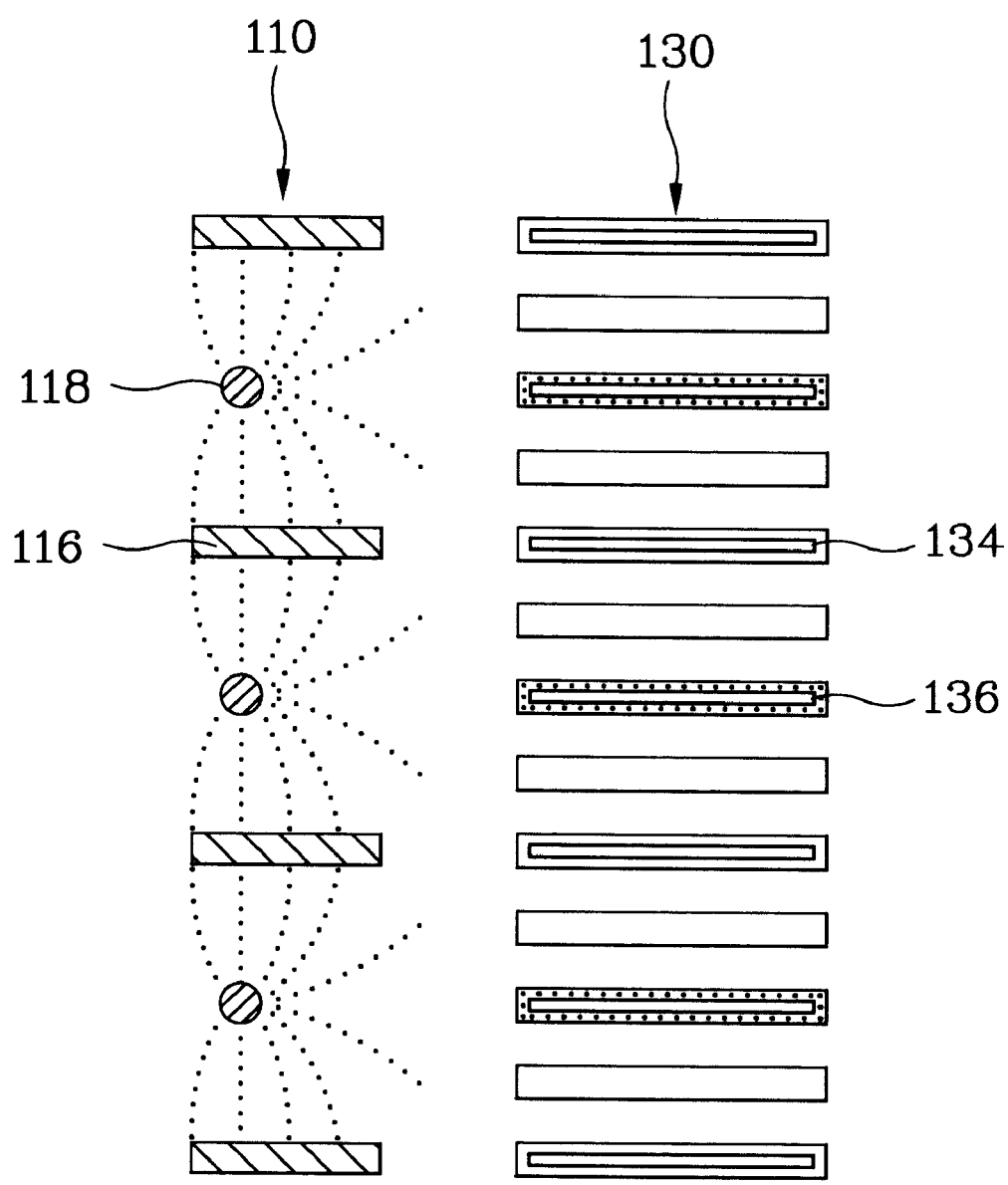
FIG. 5 illustrates a cross section of an electrostatic precipitator in accordance with another preferred embodiment of the present invention.

FIG. 5 illustrates a cross section of an electrostatic precipitator in accordance with another preferred embodiment of the present invention, referring to which the another embodiment electrostatic precipitator will be explained. This embodiment, being a modified version of the first embodiment, is identical to the first embodiment in that the photo-energy source which activates the photo-catalyst is not provided separately. In this embodiment, a separate photo-catalyst filter is not used, but a component of the background art electrostatic precipitator is designed to include the photo-catalyst in achieving the object of the present invention. Of course, the component should be a component disposed at a distance within the reach of the photo-energy source which activates the photo-catalyst.

According to the embodiment shown in FIG. 6, the photo-catalyst is contained in the positive electrodes 136 in the collecting unit 130, for being activated by a photo-energy emitted from the discharge electrodes 118 in the discharge unit 110. Herein, the word "contain" implies both cases of containing the photo-catalyst in one component and coating the photo-catalyst on the one component. That is, in the case of the positive electrodes coated with a resin, the photo-catalyst may be contained in the resin or the photo-catalyst may be coated on the resin, and, in the case of the positive electrodes without the resin coating, the photo-catalyst may be directly coated on the positive electrodes.

Though, in the second embodiment, a case of the photo-catalyst contained in the positive electrodes 136 in the collecting unit 130 is explained, the present invention is not limited to this. the photo-catalyst may be contained in any place wherever the photo-energy of a certain magnitude discharged from discharge electrodes 118 in the discharge unit 110 can reach and activate the photo-catalyst. For example, the photo-catalyst may be contained in the ground electrodes 116 in the discharge unit 110.

The operation and advantages of this embodiment is the same with the first embodiment, except the following additional advantages.

Because this embodiment allows fabrication of the electrostatic precipitator of the present invention by a mere containment of the photo-catalyst in one component of the background art electrostatic precipitator, an existing electrostatic precipitator can be used without any structural design change as it is. Thus, an existing production equipment can be used as it is and, on the same time, degrees of freedom in design of an electrostatic precipitator can be improved.

It will be apparent to those skilled in the art that various modifications and variations can be made in the electrostatic precipitator of the present invention without departing from the spirit or scope of the invention. Thus, it is intended that the present invention cover the modifications and variations of this invention provided they come within the scope of the appended claims and their equivalents.

What is claimed is:

1. An electrostatic precipitator comprising:
   a discharge unit including ground electrodes and discharge electrodes;

a collecting unit including collecting electrodes and positive electrodes;

a filter containing a photo-catalyst;

a voltage generating unit configured to apply a voltage to the discharge unit that causes emission of a photo-energy which activates the photo-catalyst.

2. An electrostatic precipitator as claimed in claim 1, wherein the voltage generating unit generates a DC biased pulse voltage.

3. An electrostatic precipitator as claimed in claim 1, wherein the photo-catalyst filter is a metal net coated with the photo-catalyst.

4. An electrostatic precipitator as claimed in claim 1, wherein the photo-catalyst filter is disposed between the discharge unit and the collecting unit.

5. An electrostatic precipitator as claimed in claim 1, wherein the photo-catalyst filter is mounted on a side of the collecting unit opposite the discharging unit.

6. An electrostatic precipitator comprising:

a discharge unit including ground electrodes and discharge electrodes;

a collecting unit including collecting electrodes and positive electrodes;

a voltage generating unit; and a photocatalyst, wherein the photocatalyst is contained within at least one of the discharge unit and the collecting unit, and wherein the voltage generating unit is configured to apply a voltage to the discharge unit that causes emission of a photo-energy which activates the photo-catalyst.

7. An electrostatic precipitator as claimed in claim 6, wherein the voltage generating unit is configured to apply a DC biased pulse voltage to the discharge unit.

8. An electrostatic precipitator as claimed in claim 6, wherein the photo-catalyst is contained in at least one of the positive electrodes.

9. An electrostatic precipitator as claimed in claim 6, wherein the photo-catalyst is contained in at least one of the ground electrodes.

10. An electrostatic precipitator as claimed in claim 1, wherein the filter is located in a position that allows the emitted photo-energy to activate the photo-catalyst.

11. An electrostatic precipitator as claimed in claim 6, wherein the component of the electrostatic precipitator containing the photo-catalyst is located in a position that allows the emitted photo-energy to activate the photo-catalyst.

12. An electrostatic precipitator as claimed in claim 8, wherein the photocatalyst is coated on at least one of the positive electrodes.

13. An electrostatic precipitator as claimed in claim 9, wherein the photocatalyst is coated on at least one of the ground electrodes.

14. An electrostatic precipitator, comprising:

discharge means for emitting an electrical discharge that charges particles contained in an air flow;

collecting means for collecting the charged particles in the air flow; and a photo-catalyst, wherein the discharge means causes emission of a photo-energy that activates the photo-catalyst.

15. The electrostatic precipitator of claim 14, wherein the photo-catalyst is attached to a component of the electrostatic precipitator.

16. The electrostatic precipitator of claim 14, wherein a voltage applied to the discharge means causes the emission of photo-energy.

17. The electrostatic precipitator of claim 16, wherein the voltage is a DC biased pulse.

18. The electrostatic precipitator of claim 14, wherein the photo-catalyst is contained in a filter.

19. The electrostatic precipitator of claim 18, wherein the filter is located sufficiently close to the discharge unit that the emitted photo-energy activates the photo-catalyst.

20. An electrostatic precipitator as claimed in claim 6, further comprising a filter unit, located between the discharge unit and the collecting unit, wherein the discharge unit contains a photo-catalyst.

21. The electrostatic precipitator of claim 14, further comprising filter means for filtering the air flow, wherein the filter means is located between the discharge means and the collecting means, and wherein the photo-catalyst is located on the filter means.

* * * * *